Figure 1:
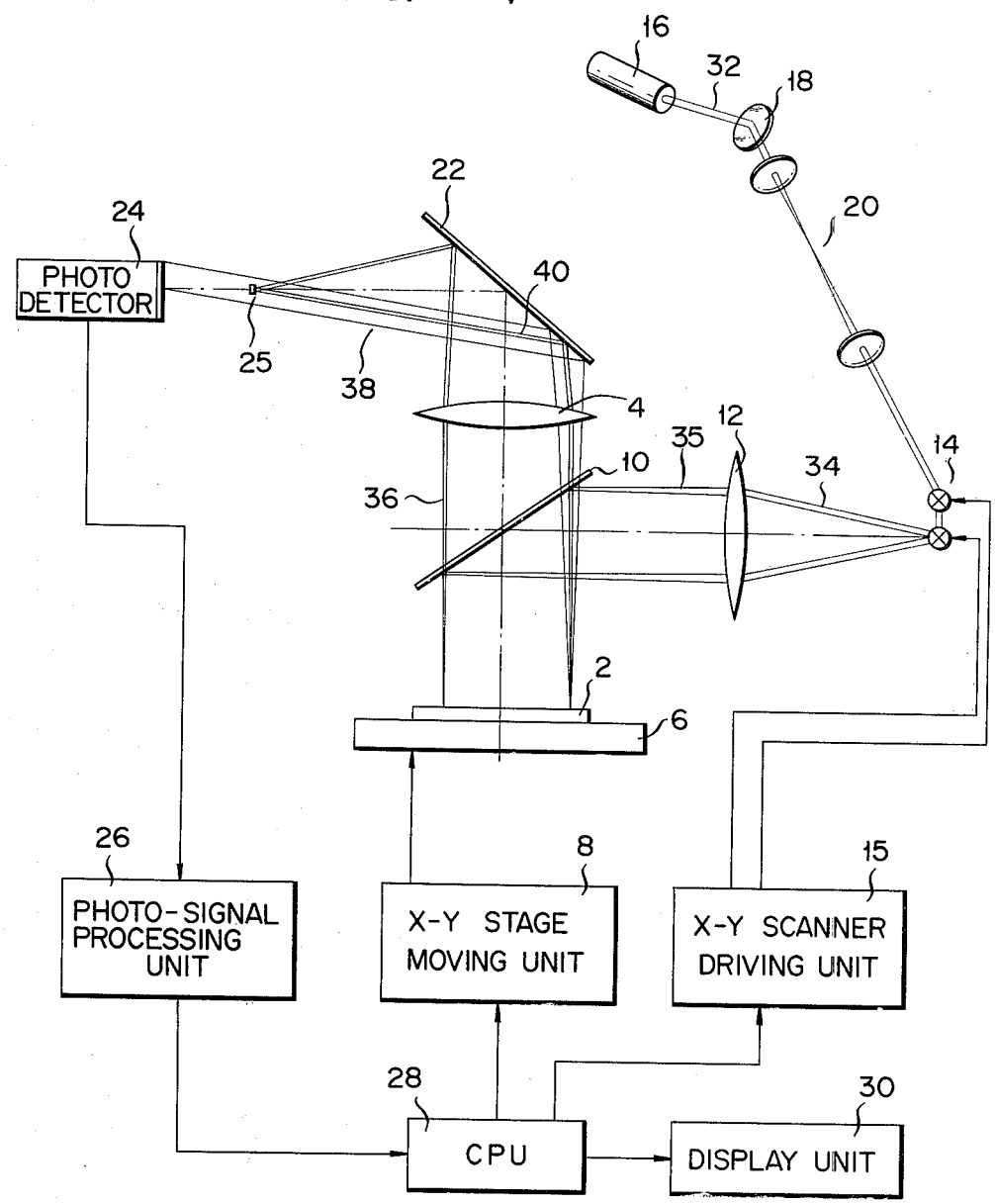

United States Patent [19]

Murakami et al.

[11] 4,330,205

[45] May 18, 1982

[54] OPTICAL APPARATUS FOR MEASURING THE SIZE AND LOCATION OF OPTICAL IN AN ARTICLE

[75] Inventors: Teruo Murakami, Yokohama; Kiyoshi Yamada, Tokyo; Masana Minami, Kawasaki, all of Japan

[73] Assignee: Tokyo Shibaura Denki Kabushiki Kaisha, Kawasaki, Japan

[21] Appl. No.: 109,217

[22] Filed: Jan. 3, 1980

[30] Foreign Application Priority Data

Jan. 12, 1979 [JP] Japan .................................. 54-1287
Jan. 24, 1979 [JP] Japan .................................. 54-6120

[51] Int. Cl.³ ...................... G01B 11/30; G01N 21/47
[52] U.S. Cl. .................................... 356/237; 250/572; 356/446
[58] Field of Search ............... 356/237, 239, 240, 371, 356/446, 430, 431; 250/563, 572

[56] References Cited

U.S. PATENT DOCUMENTS

| | | | |
|---|---|---|---|
| 3,565,568 | 2/1971 | Hock .................................... | 356/448 |
| 3,790,287 | 2/1974 | Cuthbert et al. ..................... | 356/446 |
| 3,795,452 | 3/1974 | Bourdelais et al. ................. | 356/237 |
| 3,892,494 | 7/1975 | Baker et al. ......................... | 356/239 |

OTHER PUBLICATIONS

"Particle Sizing Using Laser Interferometry"; Roberds; Applied Optics., vol. 16, #7, Jul. 1977, pp. 1861–1868.

"Laser Beam Reading of Video Records", Velzel, Applied Optics., vol. 17, #13, Jul. 1978, pp. 2029–2036.

*Primary Examiner*—Vincent P. McGraw
*Attorney, Agent, or Firm*—Oblon, Fisher, Spivak, McClelland & Maier

[57] ABSTRACT

In an optical apparatus for inspecting optical defects, a laser beam generated from a laser unit is converted by a collimator lens into a light beam having a suitable diameter. An X-Y scanner for two-dimensionally scanning the light beam is situated at a forward focal point of a scanning lens. The light beam passed through the scanning lens is converged substantially in parallel with an optical axis of the scanning lens and is reflected by a semi-transparent mirror and is vertically projected onto a flat surface to be inspected of an article situated substantially at a backward focal point of the scanning lens. Thus, on the surface to be inspected of the article there is given a projected beam spot having a larger diameter than that of the relevant circle of least confusion. The light rays reflected by the article surface to be inspected are converged by a converging lens the forward focal point of which is located on the said article surface. The light rays regularly reflected by that article surface are converged by the converging lens to a spatial filter and one cut off by the same. Only light rays irregularly reflected by the article surface enters a photo-detecting unit through the spatial filter.

3 Claims, 2 Drawing Figures

OPTICAL APPARATUS FOR MEASURING THE SIZE AND LOCATION OF OPTICAL IN AN ARTICLE

This invention relates to an optical apparatus which inspects an article having a flat surface to determine the size and location of any optical defects existing on the flat surface.

An optical apparatus is known which measures by inspection the size and location of optical defects in flat surfaces of an article, including pits or projections formed on the same, dust caused to attach to the same, and the like (hereinafter, simply referred to as "optical defects"). This type of conventional optical apparatus scans the flat surface of an article by means of laser beams, thereby to inspect the conditions thereof by light reflected by or transmitted through the article. Methods for such inspection or measurement include measuring the irregularly reflected lights and measuring the regularly reflected lights. When laser beams enter a certain portion of the flat surface of the object, if it has optical defects, they would be irregularly reflected at the defective portion and scattered. This method for measuring the size and location of such optical defects by detecting the scattered lights or irregularly reflected light is given as the above-mentioned irregularly reflected light measuring method. In contrast, the regularly reflected light of a light beam having entered a surface portion having optical defects attenuates, as a result of the light beam being partially scattered, relative to that of a light beam having entered a portion of the optical flat surface having no optical defects at all. Thus, by measuring the regularly reflected light the location of the optical defects can be measured and also the size thereof determined from the amount of attenuation as measured. This is the above-mentioned regularly reflected light measuring method. Usually, the former scattered light measuring method is adopted for a conventional optical apparatus for inspecting optical defects. Because, in the latter method, it is difficult to accurately detect the amount of attenuation and the finer the defects are the more difficult it is to discriminate the detection signal from the noise components.

Nextly, the method for scanning, in order to detect the surface portion of an object having optical defects, the object surface over the entire area thereof by a beam spot thereon produced when laser beams have been projected to that surface includes the following three methods. (1) One to fix in position an object to be inspected and optically scan the flat surface of the object by two-dimensional operation of laser beams, (2) one to horizontally rotate a stage about the center thereof on which is installed an object to be inspected and linearly or one-dimensionally move the stage or the optical system involved, and (3) one to linearly or one-dimensionally scan the flat surface of the object by linear operation of laser beams and also linearly or one-dimensionally move the object-installed stage at right angles to the scanning direction. In the method (1), since the positions of a lens for focussing the scattered lights and a photo detector are fixed on the irregular light rays path and are not arranged on the regular light rays path, the distance between the light projected point on the flat surface and the focussing lens is not kept constant, so that the value of detection unpreferably varies with the position of each defect. In the method (2), since the object to be inspected is in rotation during examination, the defects inside the center-of-rotation area on the flat surface are exposed to light beam longer time than those on the ambient area to that area even if the former defects are of the same size as the latter. As a result, the value of detection of the former may be different from that of the latter. Further, in the method (3), since the stage is mechanically moved in a linear fashion, the speed of the inspection is low.

Further, only the optical defects on the flat surface of an object should naturally be inspected by exposure thereon of laser beams. In spite of this, if optical elements arranged on the path of those laser beams and on the path of lights scattered on the flat surface of the object have optical defects, it would be possible that the detection signal is mixed with signals, as a noise, on the defects of such elements which are not the object to be inspected.

The object of the invention is to provide an optical apparatus which is capable of accurately and quickly inspecting optical defects on an article to be inspected.

According to the invention, there is provided an optical apparatus for inspecting optical defects which comprises (a) a laser unit for generating a laser beam, (b) a collimating means for converting the laser beam into a light beam consisting of parallel light rays and having a diameter of a suitable size, (c) an X-Y scanner for subjecting the light beam to two-dimensional scanning, (d) a driving means for driving the X-Y scanner, (e) a light beam projection lens system having a forward focal point at the X-Y scanner to converge a light beam incident to the system and to eject it substantially in parallel with an optical axis thereof, (f) a table means having a flat surface to be inspected which is to be positioned substantially at the backward focal point of the system and supporting an article to be inspected on which flat surface is given a projected light beam spot of a specified size, (g) a light directing means arranged in a light beam path between the table means and the light beam projection lens system to direct the light beam projected from the light beam projection lens system in the direction which is vertical to a surface to be inspected of the article, (h) a converging lens system having a forward focal point on the surface of the article and having an optical axis vertical to the inspected surface, whereby to converge light rays obtained by one of the ways of being reflected by and being transmitted through the surface, (i) a spatial filter means positioned at a backward focal point of the converging lens system to transmit therethrough only light rays obtained by one of the ways of being irregularly reflected and being scattered by the article, (j) a photodetecting unit for detecting the light rays transmitted through the spatial filter, and (k) an analyzing means for analyzing, to obtain the size and location of, defects on the article in accordance with output signals from the photo-detecting unit and driving signals from the X-Y scanner driving means.

Figure 2:
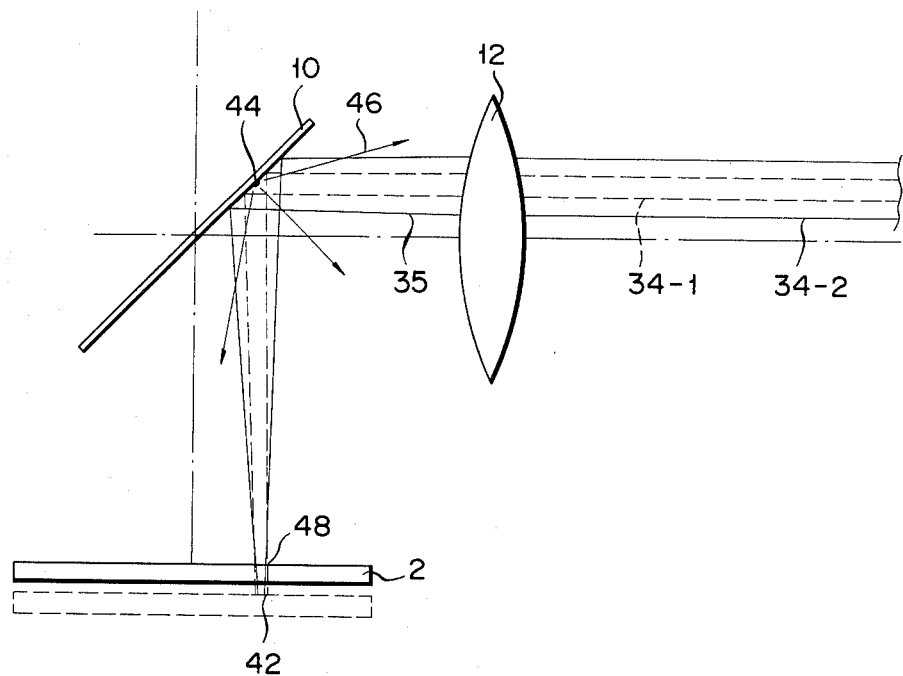

This invention can be more fully understood from the following detailed description when taken in conjunction with the accompanying drawings, in which:

FIG. 1 schematically shows an optical apparatus for inspecting optical defects according to an embodiment of the invention; and FIG. 2 is an enlarged view of a principal part of the apparatus illustrated in FIG. 1, for the purpose of explaining an effect of the invention to minimize by relatively enlarging the diameter of an incident light beam the undesirable effect due to, for example, dust in the optical system and thus improve the detection accuracy.

In FIG. 1 there is schematically shown an optical apparatus for inspecting optical defects according to an embodiment of the invention. As shown, an article 2 to be inspected is put on an X-Y stage 6 in such a manner that a surface to be inspected of the article faces a converging lens 4 for converging light rays reflected by that surface. The X-Y stage 6 is installed so that it can be moved by an X-Y stage moving unit 8. This unit can move the stage 6 in an X direction, for example, vertical to the drawing sheet and in a Y direction intersecting the X direction at right angles thereto and taken along the plane of the X-Y stage 6. The converging lens 4 has an optical axis which intersects the surface of the X-Y stage 6 on which the article 2 is put, at right angles to that surface. The converging lens 4 has a forward focal point at the surface to be examined of the article 2. Between the lens 4 and the X-Y stage 6 is disposed a half-mirror or semitransparent mirror 10, which permits reflection of the incident light beam onto the surface to be inspected of the article or object 2 and permits transmission therethrough of the light rays reflected by that article surface, so as to define an angle of substantially 45° with respect to the relevant surface of the X-Y stage 6. A scanning lens 12 is disposed in opposing relationship to a light reflection surface of the semitransparent mirror 10. The scanning lens 12 is disposed in such a manner that its optical axis defines an angle of substantially 45° with respect to the face of the semitransparent mirror 10 and intersects the optical axis of the converging lens 4 at right angles thereto. The scanning lens 12 is disposed so that its backward focal point may be disposed substantially on the surface to be inspected of the article or object 2, or preferably so that the surface to be inspected of the article may be situated near a circle of least confusion cross-sectionally taken with respect to the light beam converged by the scanning lens 12, as later described. At a forward focal point of the scanning lens 12 is disposed an X-Y scanner 14 such as a combined mirror. The X-Y scanner 14 is driven by an X-Y scanner driving unit 15 and can scan in the X and Y directions the light beam converted onto the surface to be inspected of the object 2 while entering the same vertically thereto. A mirror 18 and a collimator lens unit 20 are arranged between the X-Y scanner 14 and a laser unit 16 for generating the light beam which enters the X-Y scanner 14. The collimator lens unit 20 is provided for arranging the light beam reflected by the mirror 18 into a light beam of a suitable diameter. The collimator lens unit 20 converts such reflected light beam into a light beam consisting of parallel light rays and preferably having a relatively large diameter as later described in connection with FIG. 2.

A reflecting mirror 22, as shown in FIG. 1, is disposed on the path of the light rays having passed through the converging lens 4. On the path of the light reflected from the reflecting mirror 22 is disposed a light receiving face of a photo-detector 24 for detecting the amount of the reflected light entering this detector through that path. At a backward focal point of the converging lens 4 situated on an optical axis extending to the mirror 22 and further to the photo-detector 24 after passing through the converging lens 4 is provided a spatial filter 25 of a suitable size which shields the light rays regularly reflected from the surface to be inspected of the object article 2. The photo-detector 24 is connected to a photo-signal processing unit 26 for processing a detection signal photo-electrically converted by the photo-detector 24. A central processor unit (hereinafter, referred to simply as "CPU") 28 is provided which gives the size and location of the detected defects on the basis of the data processed by the photo-signal processing unit 26 and the location data fed from the X-Y scanner driving unit 15 and the X-Y stage moving unit 8. A display unit 30 such as a printer is further provided which displays the processed result obtained from the CPU 28.

According to the above-mentioned embodiment, a laser beam 32 generated from the laser unit 16 is reflected by the mirror 18. The laser beam 32 is converted by the collimator lens 20 into a light beam 34 consisting of a pencil of parallel light rays having a relatively large diameter, which light beam 34 then enters the X-Y scanner 14. The light beam 34 scanned by the X-Y scanner 14 is converged by means of the scanning lens 14 to enter the semitransparent mirror 10 and, after having been reflected by the mirror 10, is projected onto the surface to be inspected of the object 2 substantially vertically thereto. Thus, a beam spot of a specified size is projected onto that surface. When there is no defect on the surface to be inspected of the object falling within the projected spot, the light beam 35 projected is regularly reflected by the surface to be inspected of the object 2. The light rays thus regularly reflected advance substantially in parallel with the optical axis of the converging lens 4 and pass through the semitransparent mirror 10 to enter the converging lens 4. The light beam or light rays 36 having entered the converging lens 4 substantially in parallel with the optical axis thereof are converged by the converging lens 4 onto the forward focal point thereof and are cut off by the spatial filter 25. As a result, those light rays are almost not allowed to enter the optical detector 24. This means that no detection signal is supplied to the photo-signal processing unit 26. Since, however, the CPU 28 has already sensed the location of the object given the projected spot on the basis of the scanning signals applied to the X-Y scanner driving unit 15 and X-Y stage moving unit 8, we can be aware that no defects are present on that location of the object.

When, on the other hand, any defect is present on the location of the object 2 to which the beam spot is given, we obtain the light rays 38 irregularly reflected from the region in which such defect is present. The light rays irregularly reflected scatteringly advance and enter the converging lens 4 through the semitransparent mirror 10. Such light rays irregularly reflected, however, are indeed paralleled by the converging lens 4 but part thereof is only cut off by the spatial filter 25 with the remaining allowed to enter the photo-detector 24. The amount of such light rays irregularly reflected correspond to the size of the defect on the surface to be inspected of the article while the amount of light rays entering the photo-detector 24 corresponds to the size of the defect on the surface of the object. Therefore, the photo-detector 24 applies a signal corresponding to the defect to the photo-signal processing unit 26. This unit applies to the CPU 28 a signal indicating the defect size from which CPU we can be aware of the location of the defect as well as the size thereof. The area occupied by the location of the object article having the projected beam spot includes non-defective portion as well as such defective portion. Light rays 40 reflected from such non-defective portion are cut off by the optical filter 25 as mentioned above.

As a result of the light beam 34 being scanned by the X-Y scanner 14 and the X-Y stage 6 being moved, the light beam 34 sweeps over the surface to be inspected of the object 2 with high speed owing to the co-operation of both said scanning and said movement. As seen, in order to inspect the object surface with high speed it is essential that the direction in which the light beam 34 scanned by the X-Y scanner 14 sweeps over the object surface to be inspected is opposite to that in which the X-Y stage 6 is moved. On the basis of such high-speed inspection the CPU 28 can operate quickly to cause the display unit 30 to display the size and location of the defects.

Since the optical apparatus for inspecting optical defects according to the invention has the above-mentioned construction, it has the following merits.

(1) The surface to be inspected of the object 2 can be inspected with high speed or within a short time. Because, according to the invention, the light beam 34 is led to scan in the X-Y direction and further the stage 6 can also be moved in the X-Y direction.

(2) Since the directions of scanning by the light beam 34 and of the stage movement are both the X-Y direction, namely, two-dimensional direction, the location of defective portions of the object surface to be inspected can be accurately and easily detected. Further, for the same reason, signal processing can also be reliably effected in regard to errors of doubly counting the same defect.

(3) Since the light beam on light rays 40 regularly reflected by the surface to be inspected of the object 2 are cut off by the spatial filter 25 with the result that only light rays irregularly reflected by defective portions of that surface are detected by the photo-detector 24, the size and location of such defective portion can be accurately detected even if such is a minute particle. Namely, the noise component in the detection signal can be made sufficiently small.

(4) According to the invention, light beams are substantially vertically projected onto the surface to be examined of the object article and the light rays regularly reflected thereby are converged by the converging lens 4. The optical apparatus of the invention is thus arranged to detect the size of defective surface portions by such light rays converged. Even if, therefore, such defects are present on any area of the object surface, so long as they are of the same size, the detected value or the resulting amount of light rays becomes the same. In other words, the apparatus of the invention can accurately detect the size of such defects regardless of their location.

The above-mentioned embodiment has shown as an example the case where the surface to be inspected of the object 2 is a flat surface which is capable of reflecting lights (and which means a surface of an article incapable of absorbing lights of specified wavelength). The object 2 referred to in the above-mentioned embodiment can be a transparent article (which, we mean, is transparent with respect to lights of specified wavelengths). In this case, detection may be made of only light rays scattered by the transparent article. In the case of the object 2 being such transparent article, however, it can not be determined whether or not the detected defects are the defects produced inside the article, or on which side of the front and back surfaces such defects are existent.

In the above-mentioned embodiment, the light beam projection system consisting of the optical elements 12, 14, 16, 18, 32 and 34 may be interchanged in position with the light rays detection system consisting of the optical elements 4, 22, 24 and 25. Namely, no inconvenience would occur even if the scanning lens 12 is interchanged in position with the converging lens 4 and the corresponding optical elements are rearranged correspondingly.

In the above-mentioned embodiment it has been stated that it is preferable that the laser beam 32 generated from the laser unit 16 be converted by the collimator lens 20 into a light beam 34 of a relatively large diameter and the light beam 35 converted by the scanning lens 12 be projected onto the surface to be inspected of the object 2 by being adjusted thereto of a position near a circle of least confusion cross-sectionally taken with respect to the beam 35. The reason for this will be stated referring to FIG. 2.

In this system, the size of a projected spot on the surface to be inspected of the object article 2 is determined principally in accordance with the size of a defect to be detected. If that defect has a size of, for example, about 2~3 $\mu$m, the size of the projected spot would be determined to about 100 $\mu$m. This determination is made in consideration of the scanning speed of the X-Y scanner 14, the nature of the object surface to be examined, etc. As well known, the light beam 38 converged by the scanning lens 12, as shown in FIG. 2, has the smallest diameter at the circle of least confusion 42 taken at the focal point of the lens 12. The position of the scanning lens 12 is generally determined so that such circle of least confusion 42 can be taken on the surface to be inspected of the object article 2, as a projected spot. When the size of such projected spot is determined, the focal distance of the scanning lens 12, the position of disposing the same, the diameter of a light beam 34-1 incident to the same, etc. will be determined. The focal distance of the scanning lens 12 is only given a relatively low degree of freedom on design since the determination of such focal distance should be made in connection with the position of the X-Y scanner 14 and that of the surface to be inspected of the object 2. Accordingly, when the size of the projected spot or the circle of least confusion is determined, then will be determined the diameter of the light beam 34-1 incident to the scanning lens 12. It is to be noted here that the following relation can be established between the diameter $W_{EX}$ of the circle of least confusion and the diameter $W_{IN}$ of the light beam 34-1 incident to the scanning lens 12.

$$W_{EX} \simeq (f\lambda)/(\pi W_{IN})$$

where f represents the focal distance of the scanning lens 12 and $\lambda$ the wavelength of the laser beam 34-1.

When as mentioned above, the circle of least confusion 42 of a predetermined size has been given to coincide with the object surface to be inspected, then the diameter of the light beam 34-1 incident to the scanning lens 12 is determined. If the diameter of the light beam 34-1 is much larger than the size of the defect involved, no problem will arise. If, however, that beam diameter is not much larger than the size of the defect 44 and if it is such a relatively fine light beam as shown by an arrow 34-1 in FIG. 2, the light rays 46 contained in such light beam are likely to be scattered due to the presence of defects 44 such as dust, damages, etc. in the optical system which the light beam passes through. Thus, the detecting accuracy is likely to decrease.

In the above-mentioned embodiment of the invention, therefore, a light beam 34-2 of a relatively large diameter is used for reducing the proportion of such scattered light rays 46 even if there occurs such scattering. Namely, the collimator 20 according to the embodiment of the invention converts the light beam 32 incident thereto into the light beam 34-2 of a relatively large diameter which, even if the light beam 32 should be scattered due to the existence of defects 44 in the optical system, would not be affected by such scattering. As a result, the circle of least confusion 42 obtained by converging the light beam 34-2 by means of the scanning lens 12 becomes smaller than a specified value. However, if, as in the above-mentioned embodiment, the position of the object surface to be inspected, i.e., the position of the scanning lens 12, as indicated by solid lines in FIG. 2, is adjusted and, as shown in FIG. 2, shifted to a suitable position near the location of the least confusion circle 42, then it becomes possible that the projected beam spot 48 of a predetermined size is given to the object surface to be inspected.

As stated above, the optical apparatus of the invention enables the defects on the surface to be inspected of the object to be accurately and quickly inspected without being substantially affected by the presence of defects in the optical system.

What we claim is:

1. An optical apparatus for inspecting optical defects comprising:
   (a) a laser unit for generating a laser beam;
   (b) a collimating means for converting said laser beam into a light beam consisting of parallel light rays and having a diameter of a predetermined size;
   (c) an X-Y scanner for subjecting said light beam to two-dimensional scanning;
   (d) a driving means for driving said X-Y scanner;
   (e) a table means adapted for supporting an article having a flat surface to be inspected;
   (f) a light beam projection lens system having a forward focal point and a backward focal point, the forward focal point being positioned at said X-Y scanner to converge the light beam from the collimating means and adapted to project it substantially in parallel with an optical axis thereof onto the flat surface of said article, the projected light beam defining a beam spot having a diameter determined in accordance with the defect to be detected and larger than that of the circle of least confusion of the converged light beam, the light beam converted by said collimating means having a diameter determined in accordance with the diameter of the beam spot;
   (g) a light directing means arranged in a light beam path between said table means and said light beam projection lens system and adapted to direct the converged light beam in a direction which is perpendicular to the article surface;
   (h) a converging lens system having a forward focal point, a backward focal point and an optical axis adapted to intersect the article surface at a right angle, the forward focal point adapted to be positioned at said article surface such that the light rays of the light beam spot are converged on the article surface;
   (i) a spatial filter means positioned at the backward focal point of said converging lens system and adapted to transmit therethrough only light rays irregularly reflected or scattered by said article,
   (j) a photo-detecting unit for detecting the light rays transmitted through said spatial filter, and
   (k) an analyzing means for analyzing, to obtain the size and location of, defects on said article in accordance with output signals from said photodetecting unit and driving signals from said X-Y scanner driving means.

2. The optical apparatus according to claim 1, which further comprises a moving means for moving said table means and said analyzing means analyzes the position of said article in accordance with a moving signal from said moving means and a driving signal from said driving means.

3. The optical apparatus according to claim 1 in which said directing means is a semi-transparent mirror which reflects a light beam from said light beam projection lens system and transmits the light rays reflected from said article.

* * * * *